(12) United States Patent
Tokko et al.

(10) Patent No.: US 8,777,865 B2
(45) Date of Patent: Jul. 15, 2014

(54) BLOOD PRESSURE INFORMATION MEASUREMENT DEVICE

(75) Inventors: Yoshihide Tokko, Kyoto (JP); Yukiya Sawanoi, Nara (JP)

(73) Assignee: Omron Healthcare Co., Ltd., Kyoto (JP)

( * ) Notice: Subject to any disclaimer, the term of this patent is extended or adjusted under 35 U.S.C. 154(b) by 422 days.

(21) Appl. No.: 13/188,667

(22) Filed: Jul. 22, 2011

(65) Prior Publication Data

US 2011/0282220 A1 Nov. 17, 2011

Related U.S. Application Data

(63) Continuation of application No. PCT/JP2009/070736, filed on Dec. 11, 2009.

(30) Foreign Application Priority Data

Jan. 23, 2009 (JP) ................................ 2009-013268

(51) Int. Cl.
| | |
|---|---|
| *A61B 5/02* | (2006.01) |
| *A61B 5/021* | (2006.01) |
| *A61B 5/0225* | (2006.01) |

(52) U.S. Cl.
CPC ......... *A61B 5/02255* (2013.01); *A61B 5/02141* (2013.01)
USPC ........................................................ 600/490

(58) Field of Classification Search
USPC .................... 600/485, 490, 493, 494
See application file for complete search history.

(56) References Cited

U.S. PATENT DOCUMENTS

| | | | | |
|---|---|---|---|---|
| 4,524,777 A | * | 6/1985 | Kisioka et al. | 600/490 |
| 7,524,291 B1 | * | 4/2009 | Nakagawara | 600/499 |
| 2002/0026121 A1 | * | 2/2002 | Kan | 600/500 |

FOREIGN PATENT DOCUMENTS

| | | |
|---|---|---|
| EP | 2 047 795 A1 | 4/2009 |
| JP | 54-050175 A | 4/1979 |
| JP | 06-231475 A | 8/1994 |
| JP | 2001-017400 A | 1/2001 |
| JP | 2008-036004 A | 2/2008 |
| WO | 2008/015921 A1 | 2/2008 |

OTHER PUBLICATIONS

International Search Report issued in PCT/JP2009/070736 mailed on Jan. 19, 2010, with English translation thereof, 2 pages.

* cited by examiner

*Primary Examiner* — Navin Natnithithadha
*Assistant Examiner* — Etsub Berhanu
(74) *Attorney, Agent, or Firm* — Osha Liang LLP

(57) ABSTRACT

A blood pressure information measurement device includes a servo control unit for performing a servo control of a pressure adjustment unit so that a value of an arterial volume signal matches a control target value and a fluctuation detection unit for detecting rapid fluctuation of the arterial volume signal at an initial stage during a period of the servo control. The fluctuation detection unit determines that the rapid fluctuation occurred when a control deviation representing a level of the arterial volume signal having the control target value as a reference becomes greater than or equal to a predetermined magnification of a reference deviation. The blood pressure information measurement device further includes an adjustment processing unit for adjusting a control amount of the pressure adjustment unit by the servo control unit so that an excessive response is not made when the rapid fluctuation is detected by the fluctuation detection unit.

8 Claims, 10 Drawing Sheets

| Time data | Blood pressure data |
|---|---|
| 1 | BD(1) |
| 2 | BD(2) |
| 3 | BD(3) |
| 4 | — |
| 5 | BD(5) |
| 6 | — |
| 7 | BD(7) |
| 8 | BD(8) |
| 9 | BD(9) |
| ⋮ | ⋮ |
| N | BD(n) |

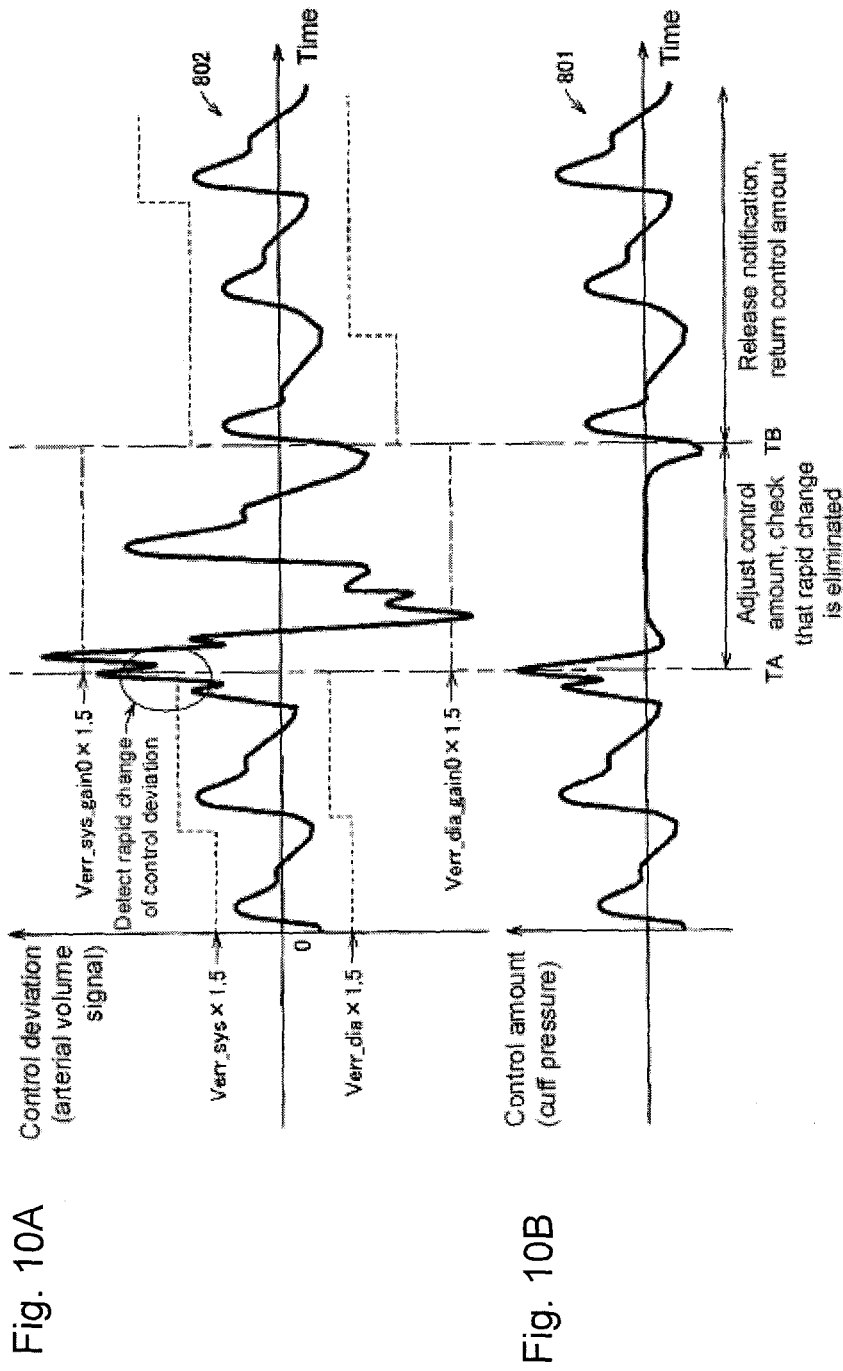

BLOOD PRESSURE INFORMATION MEASUREMENT DEVICE

TECHNICAL FIELD

The present invention relates to blood pressure information measurement devices, and in particular to a blood pressure information measurement device capable of measuring a blood pressure using a volume compensation method.

BACKGROUND ART

Blood pressure measurement by the volume compensation method has been conventionally developed as a method of non-invasively measuring the blood pressure easily and conveniently. The volume compensation method described in Japanese Unexamined Patent Publication No. 54-50175 (patent document 1) is as follows. That is, the artery is compressed by the cuff from ex vivo, and the volume of the artery pulsating in synchronization with the heart rate is constantly maintained constant to have the pressure (cuff pressure) for compressing the measurement site and the inner pressure of the artery of the measurement site, that is, the blood pressure at equilibrium. The blood pressure value is continuously obtained by detecting the cuff pressure when the equilibrium state is maintained.

In such volume compensation method, the arterial volume signal is fed back, and the servo control is carried out so that the arterial volume is always constant, that is, so that the arterial volume value matches the control target value (volume value when artery is in no-load state). Therefore, the compression degree to the measurement site changes according to the detected arterial volume signal during the blood pressure measurement period.

Japanese Unexamined Patent Publication No. 2001-17400 (patent document 2) describes a method of detecting rapid increase of the pressure pulse wave or the blood pressure.

Patent Document 1: Japanese Unexamined Patent Publication No. 54-50175
Patent Document 2: Japanese Unexamined Patent Publication No. 2001-17400

SUMMARY OF INVENTION

The arterial volume signal sometimes drastically changes due to increase in blood flow or shift of the sensor when body motion, or the like occurs during the measurement. If the arterial volume signal rapidly changes, the control deviation (level of arterial volume having control target value as reference) becomes large. If the control deviation is large, response becomes an excess due to the feedback control, and an abnormal blood pressure value is displayed. Furthermore, the burden on the person to be measured increases because the measurement site is compressed at the more than necessary cuff pressure.

A method of simply providing a limit to the cuff pressure is known, but this limit is a limit for when greatly exceeding the normally assumed blood pressure value (e.g. 280 mmHg) and thus is insufficient in terms of preventing the more than necessary compression.

In the volume compensation method, the control is performed so that the arterial volume becomes constant, where the cuff pressure and the blood pressure are equivalent. Therefore, even if the rapid increase of the blood pressure is detected as in Japanese Unexamined Patent Publication No. 2001-17400 (patent document 2), this detection will be after the excessive response has already occurred. Thus, the burden on the person to be measured cannot be avoided.

Therefore, one or more embodiments of the present invention provides a blood pressure information measurement device that conforms to the volume compensation method and is capable of avoiding the excessive compression of the measurement site.

According to one or more embodiments of the present invention, a blood pressure information measurement device is a blood pressure information measurement device for measuring blood pressure information by detecting a volume of an artery, the blood pressure information measurement device including a cuff to be wrapped around a predetermined measurement site; a pressure adjustment unit for adjusting pressure of the cuff by pressurization and depressurization; a pressure detection unit for detecting a cuff pressure representing the pressure of the cuff; a volume detection unit, arranged at a predetermined position of the cuff, for detecting an arterial volume signal indicating a volume of the artery; a detection processing unit for detecting a control target value based on the arterial volume signal; a servo control unit for performing a servo control of the pressure adjustment unit so that a value of the arterial volume signal matches the control target value; a fluctuation detection unit for detecting rapid fluctuation of the arterial volume signal at an initial stage during a period of the servo control; and an adjustment processing unit for adjusting a control amount of the pressure adjustment unit by the servo control unit so that an excessive response is not made when the rapid fluctuation is detected by the fluctuation detection unit. The fluctuation detection unit determines that the rapid fluctuation occurred when a control deviation representing a level of the arterial volume signal having the control target value as a reference becomes greater than or equal to a predetermined magnification of a reference deviation.

According to one or more embodiments of the present invention, the adjustment processing unit continues the adjustment of the control amount until the rapid fluctuation of the arterial volume signal converges.

According to one or more embodiments of the present invention, the adjustment processing unit determines that the rapid fluctuation converged when the control deviation becomes smaller than a predetermined magnification of an initial control deviation before performing the servo control at an appropriate gain for a predetermined period.

According to one or more embodiments of the present invention, the detection processing unit further detects an initial cuff pressure representing a reference cuff pressure in the servo control; and the initial control deviation is an initial value which control gain is lower than the appropriate gain, and represents the control deviation when the cuff pressure is set to the initial cuff pressure.

According to one or more embodiments of the present invention, the adjustment processing unit adjusts the control amount of the pressure adjustment unit by setting the control gain to the initial value.

According to one or more embodiments of the present invention, the adjustment processing unit adjusts the control amount of the pressure adjustment unit by setting the cuff pressure to the initial cuff pressure.

According to one or more embodiments of the present invention, the reference deviation is defined in advance as the control deviation of one or more beats earlier.

According to one or more embodiments of the present invention, the rapid fluctuation of the arterial volume can be captured at the initial stage by monitoring the control deviation of the arterial volume. Therefore, the control amount of the cuff can be adjusted before excessively compressing the measurement site. As a result, the burden on the person to be measured can be alleviated.

Furthermore, the body motion sensor, or the like does not need to be separately arranged.

BRIEF DESCRIPTION OF THE DRAWINGS

FIGS. 10A and 10B are views describing the detection of the rapid change of the arterial volume and the adjustment process of the control output in one or more embodiments of the present invention.

DETAILED DESCRIPTION OF INVENTION

Figure 1:
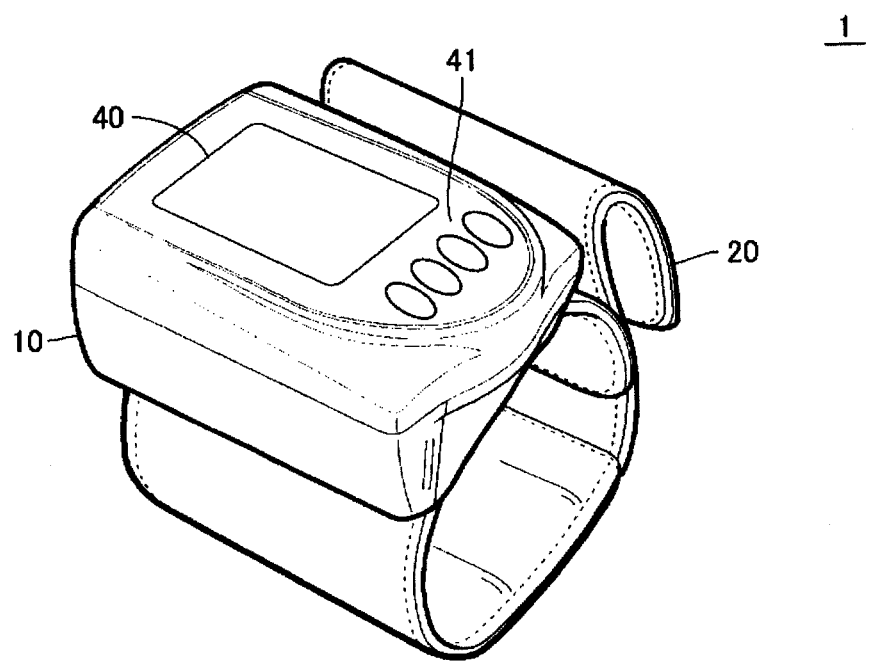
FIG. 1 is an outer appearance perspective view of a blood pressure information measurement device according to one or more embodiments of the present invention.

Embodiments of the present invention will be described in detail with reference to the drawings. The same reference numerals are denoted for the same or corresponding portions in the figures, and the description thereof will not be repeated.

The blood pressure information measurement device according to one or more embodiments of the present invention measures the blood pressure information based on the volume compensation method. According to one or more embodiments of the present invention, the "blood pressure information" is the information indicating the characteristics of the circulatory system, and includes at least the pulse wave (pulse wave signal), and also includes indices that can be calculated from the pulse wave in addition to the pulse wave such as a continuous blood pressure value (blood pressure waveform), systolic blood pressure, diastolic blood pressure, average blood pressure, pulse rate, AI (Augmentation Index) value, and the like.

The pulse wave, which is one type of blood pressure information, includes a pressure pulse wave and a volume pulse wave due to the difference in capturing target. The pressure pulse wave captures the pulse wave as the fluctuation of the cuff pressure involved in the volume change of the cuff by converting the fluctuation of the intravascular volume involved in the pulsation of the heart to the volume change of the cuff, and can be obtained based on the output from the pressure sensor. The volume pulse wave captures the pulse wave as the fluctuation of the intravascular volume involved in the pulsation of the heart, and can be obtained based on the output from the arterial volume sensor. The fluctuation of the intravascular volume can be captured as the fluctuation of the blood tissue amount in the blood vessel.

The term blood pressure information measurement device used in the present specification refers to the overall device having at least the function of acquiring the pulse wave, and more specifically, refers to a device for detecting the fluctuation of the blood tissue amount through an optical method and acquiring the volume pulse wave as it follows the volume compensation method. In this regard, the blood pressure information measurement device is not limited to a device for outputting the acquired volume pulse wave as the measurement result, and may be a device for outputting only the specific index calculated or measured based on the acquired volume pulse wave as the measurement result, or a device for outputting both the volume pulse wave and the specific index as the measurement result.

The blood pressure information measurement device according to one or more embodiments of the present invention as described below acquires the blood pressure waveform by continuously measuring the blood pressure through the volume compensation method.

<Regarding Outer Appearance and Configuration>
(Regarding Outer Appearance)

FIG. 1 is an outer appearance perspective view of a blood pressure information measurement device 1 according to one or more embodiments of the present invention. The outer appearance of the blood pressure information measurement device 1 is similar to a general apparatus for measuring blood pressure.

With reference to FIG. 1, a blood pressure information measurement device 1 includes a main body 10 and a cuff 20 to be wrapped around the wrist of a person to be measured. The main body 10 is attached to the cuff 20. A display unit 40 configured by liquid crystal or the like and an operation unit 41 for receiving instruction from the user (person to be measured) are arranged on the surface of the main body 10. The operation unit 41 includes a plurality of switches.

According to one or more embodiments of the present invention, the cuff 20 is described as being attached to the wrist of the person to be measured. However, the site (measurement site) where the cuff 20 is to be attached is not limited to the wrist and may be the upper arm.

As shown in FIG. 1 the blood pressure information measurement device 1 according to one or more embodiments of the present invention will be described using a mode in which the main body 10 is attached to the cuff 20 by way of example. However, a mode in which the separated main body 10 and the cuff 20 are connected by an air tube (air tube 31 in FIG. 2) as adopted in the upper arm type blood pressure information measurement device may be used.

(Regarding Hardware Configuration)

Figure 2:
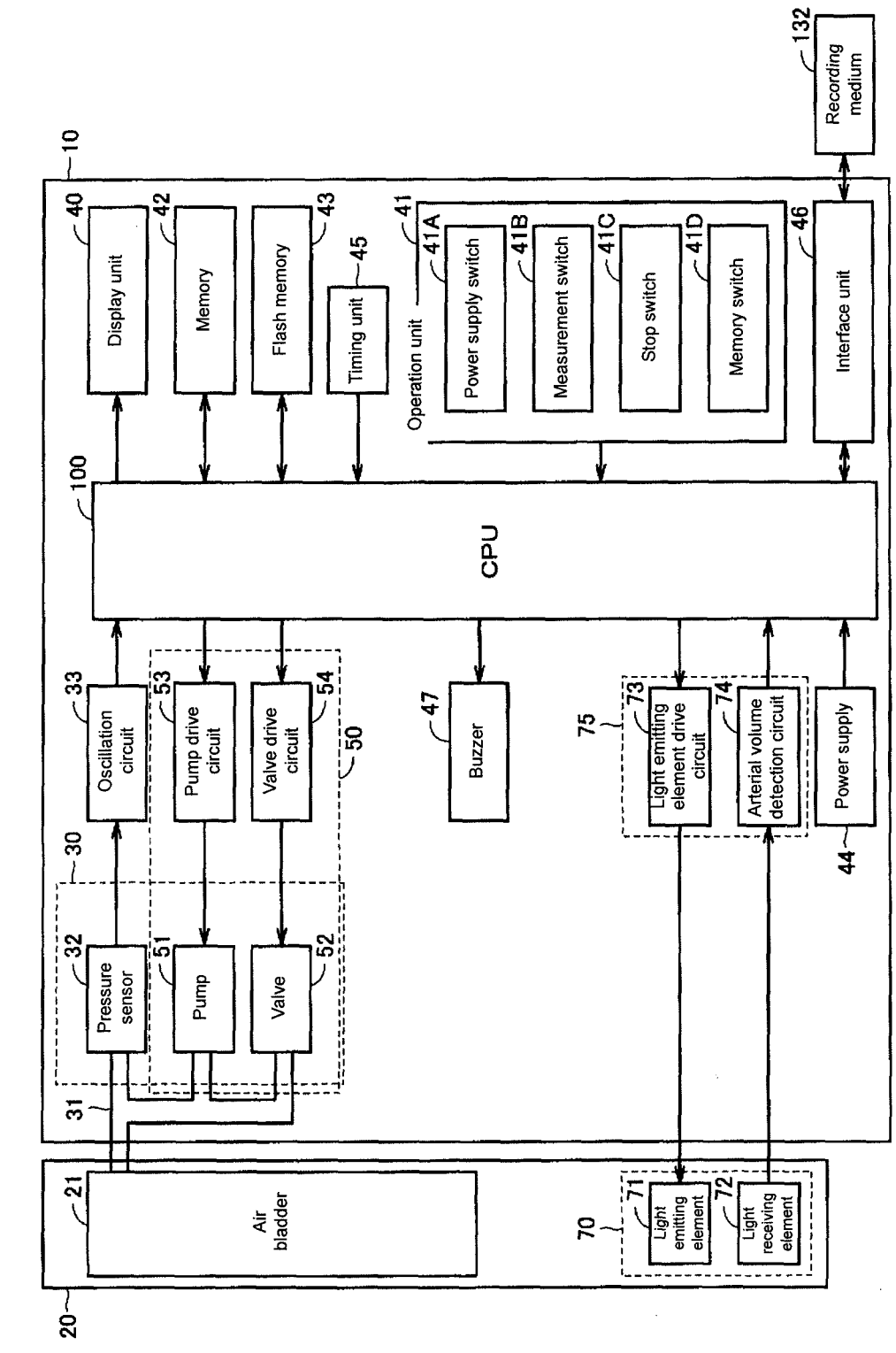
FIG. 2 is a block diagram showing a hardware configuration of the blood pressure information measurement device according to one or more embodiments of the present invention.

FIG. 2 is a block diagram showing a hardware configuration of the blood pressure information measurement device 1 according to one or more embodiments of the present invention.

With reference to FIG. 2, the cuff 20 of the blood pressure information measurement device 1 includes an air bladder 21 and an arterial volume sensor 70. The arterial volume sensor 70 includes a light emitting element 71 and a light receiving element 72. The light emitting element 71 irradiates the artery with light, and the light receiving element 72 receives the transmitted light or the reflected light of the artery of the light irradiated by the light emitting element 71. The light emitting element 71 and the light receiving element 72 are arranged at a predetermined spacing on the inner side of the air bladder 21.

The arterial volume sensor 70 merely needs to be able to detect the volume of the artery, and the volume of the artery may be detected by an impedance sensor (impedance plethysmograph). In this case, a plurality of electrodes (electrode pair for current application and electrode pair for voltage detection) for detecting the impedance of the site including the artery is arranged in place of the light emitting element 71 and the light receiving element 72.

The air bladder 21 is connected to an air system 30 through an air tube 31.

In addition to the display unit 40 and the operation unit 41, the main body 10 includes the air system 30, a CPU (Central Processing Unit) 100 for intensively controlling each unit and performing various types of calculation processes, a memory 42 for storing programs for causing the CPU 100 to perform a predetermined operation and various types of data, a non-volatile memory (e.g., flash memory) 43 for storing the measured blood pressure information, a power supply 44 for supplying power to the CPU 100, a timing unit 45 for carrying out the timing operation, an interface unit 46 for performing read and write of programs and data from a removable recording medium 132, and a buzzer 47 for emitting an alarm sound.

The operation unit 41 includes a power supply switch 41A for accepting input of the instruction for turning ON or OFF the power supply, a measurement switch 41B for accepting the instruction to start the measurement, a stop switch 41C for accepting the instruction to stop the measurement, and a memory switch 41D for accepting the instruction to read out information such as blood pressure recorded on the flash memory 43.

The air system 30 includes a pressure sensor 32 for detecting the pressure of the air bladder 21 (cuff pressure), a pump 51 for supplying air to the air bladder 21 to pressurize the cuff pressure, and a valve 52 to be opened or closed to discharge or enclose the air of the air bladder 21.

The main body 10 further includes an oscillation circuit 33, a pump drive circuit 53, and a valve drive circuit 54 in association with the air system 30.

The pressure sensor 32 is a capacitance type pressure sensor, where the capacitance value changes by the cuff pressure. The oscillation circuit 33 outputs a signal of an oscillation frequency corresponding to the capacitance value of the pressure sensor 32 to the CPU 100. The CPU 100 converts the signal obtained from the oscillation circuit 33 to pressure, and detects the pressure. The pump drive circuit 53 controls the driving of the pump 51 based on the control signal provided from the CPU 100. The valve drive circuit 54 performs the open/close control of the valve 52 based on the control signal provided from the CPU 100.

The pump 51, the valve 52, the pump drive circuit 53, and the valve drive circuit 54 configure a pressure adjustment unit 50 for adjusting the pressure of the cuff 20 by pressurization and depressurization. The device configuring the pressure adjustment unit 50 is not limited to the above. For instance, the pressure adjustment unit 50 may include an air cylinder, and an actuator for driving the air cylinder in addition to the above.

The main body 10 further includes an arterial volume measuring unit 75 for measuring the arterial volume by exchanging signals with the arterial volume sensor 70.

According to one or more embodiments of the present invention, the arterial volume measuring unit 75 includes a light emitting element drive circuit 73 and an arterial volume detection circuit 74. The light emitting element drive circuit 73 causes the light emitting element 71 to emit light at a predetermined timing in response to the command signal from the CPU 100. The arterial volume detection circuit 74 detects the arterial volume by converting the output from the light receiving element 72 to a voltage value.

The air bladder 21 is arranged in the cuff 20, but the fluid to be supplied to the cuff 20 is not limited to air and may be liquid or gel. Alternatively, it is not limited to fluid, and it may be uniform microscopic particles such as micro-beads.

(Regarding Function Configuration)

Figure 3:
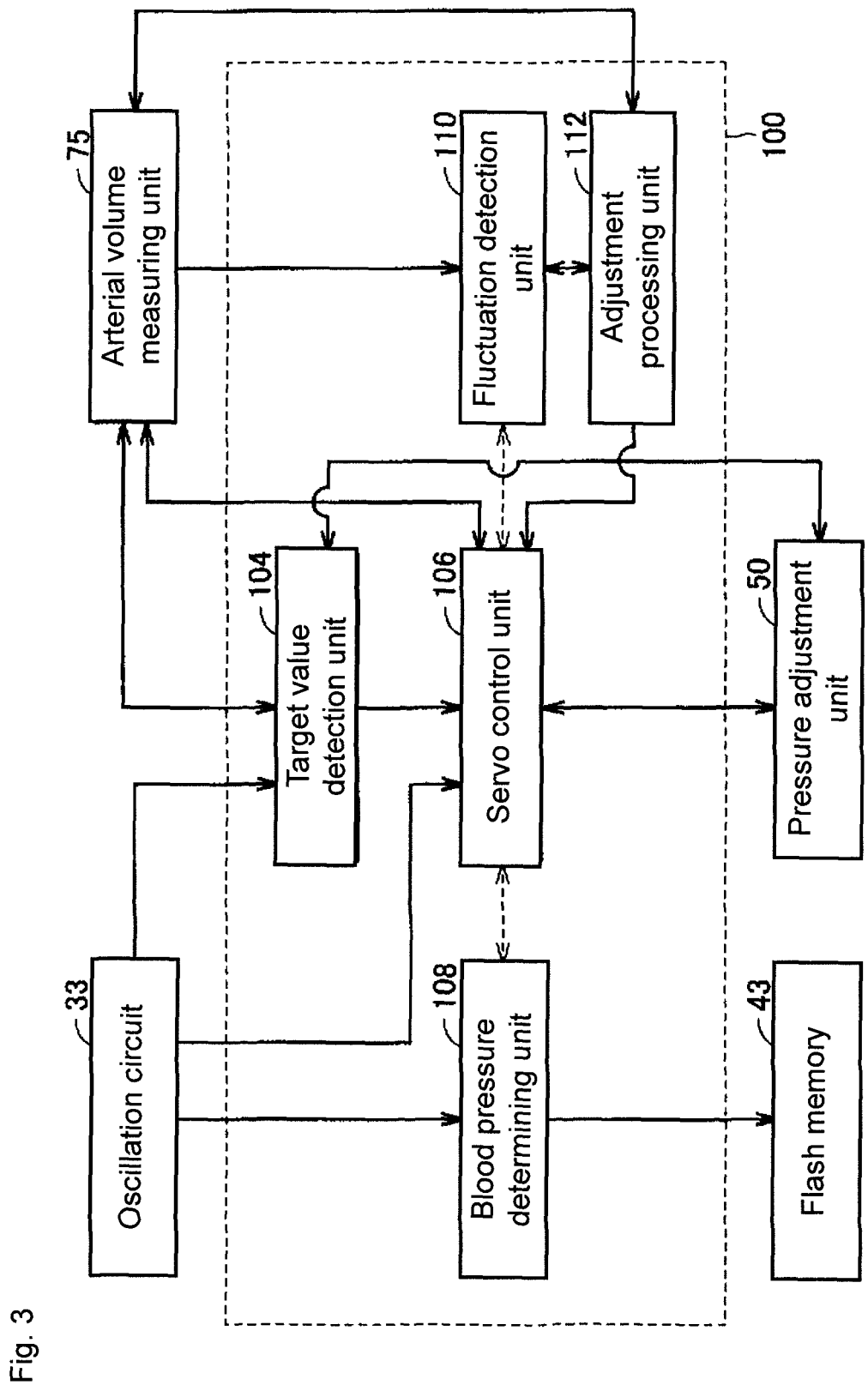
FIG. 3 is a function block diagram showing a function configuration of the blood pressure information measurement device according to one or more embodiments of the present invention.

FIG. 3 is a function block diagram showing a function configuration of the blood pressure information measurement device 1 according to one or more embodiments of the present invention.

With reference to FIG. 3, the CPU 100 includes a target value detection unit 104, a servo control unit 106, a blood pressure determining unit 108, a fluctuation detection unit 110 and an adjustment processing unit 112 as functions. In FIG. 3, only the peripheral hardware that directly exchanges signals and data with such function blocks is shown to simplify the description.

The target value detection unit 104 performs the detection process of the control target value and the initial cuff pressure in the servo control. The control target value will be briefly described using FIG. 4.

Figure 4:
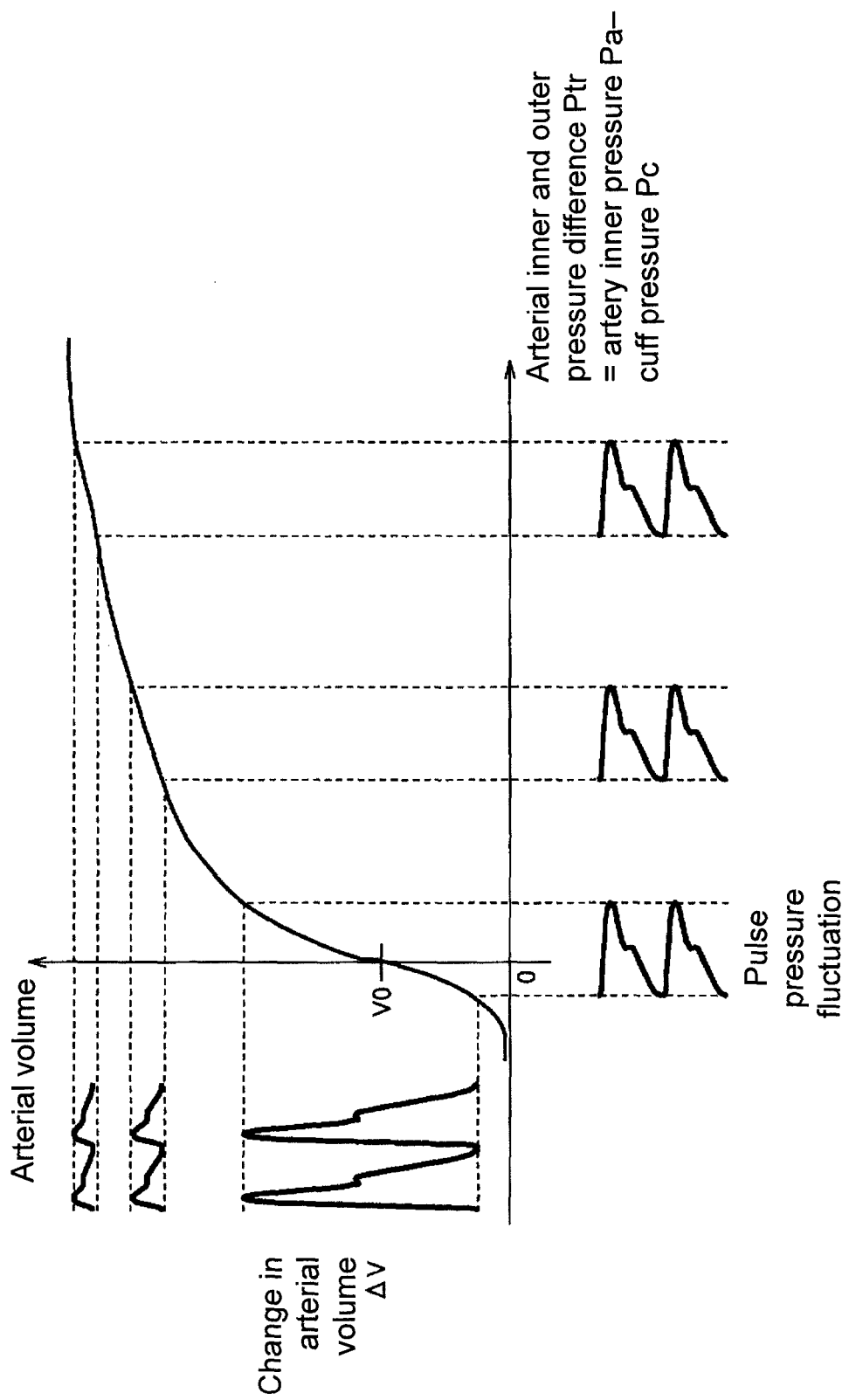
FIG. 4 is a graph showing the mechanical characteristics of the artery.

FIG. 4 is a graph showing mechanic characteristics of the artery. The graph of FIG. 4 shows a relationship of the inner and outer pressure difference Ptr and the arterial volume V with the inner and outer pressure difference Ptr taken on the horizontal axis and the arterial volume V taken on the vertical axis. The inner and outer pressure difference Ptr indicates the difference between the arterial inner pressure Pa and the cuff pressure Pc applied by the cuff from outside the body.

As shown in the graph, the mechanical characteristics of the artery generally demonstrate a strong non-linearity, where the compliance of the artery (amount of change in volume by pulsation) becomes a maximum when the inner and outer pressure difference Ptr is 0 (equilibrium state), that is, when the artery wall is in the no-load state. That is, the follow-up property (progress property) of the volume change with respect to the pressure change becomes a maximum. In the volume compensation method, the in vitro pressure (cuff pressure) is sequentially controlled to measure the blood pressure so that the arterial volume to be detected is always the capacitance value of the time point the inner and outer pressure difference Ptr becomes 0. To this end, the capacitance value of the time point the inner and outer pressure difference Ptr becomes 0, that is, the control target value ("V0") needs to be determined before the blood pressure measurement.

The target value detection unit 104 detects the control target value through a known method (e.g. Japanese Examined Patent Publication No. 1-31370, Japanese Unexamined Patent Publication No. 2008-36004). The initial cuff pressure corresponds to the cuff pressure of the time point the control target value is detected.

The servo control unit 106 is connected to the pressure adjustment unit 50, and performs the servo control so that the arterial volume matches the control target value. The method of servo control may be the PID control (refers to control of converging to control target value by combining proportional control, integral control, and derivative control) of feedback control.

The blood pressure determining unit 108 continuously determines (measures) the blood pressure during the period of the servo control. Specifically, the arterial volume signal from the arterial volume detection circuit 74 and the cuff pressure signal obtained from the oscillation circuit 33 are acquired in time series, and the cuff pressure of the time point the difference between the arterial volume value and the control target value becomes smaller than or equal to a predetermined threshold value is determined as the blood pressure.

The fluctuation detection unit 110 detects the rapid fluctuation of the arterial volume signal at the initial state during the period of the servo control. The fluctuation detection unit 110 specifically judges (estimates) that the rapid fluctuation occurred when the control deviation becomes a predetermined magnification ratio or greater than the reference deviation. The "control deviation" is the level of the arterial volume signal having the control target value as the reference. The "reference deviation" is the control deviation of one beat or more earlier, and is defined in advance as the control deviation in the previous beat according to one or more embodiments of the present invention. The reference deviation, however, is not limited to the control deviation in the previous beat, and may be an average value of the control deviations of a predetermined number of beats immediately before.

The adjustment processing unit 112 adjusts the control amount by the servo control unit 106 so that an excessive response is not made when the rapid fluctuation is detected by the fluctuation detection unit 110. The adjustment of the control amount is continued until the rapid fluctuation of the arterial volume signal converges.

The CPU 100 is assumed to be causing the light emitting element 71 to emit light at a constant interval by transmitting a command signal to the light emitting element drive circuit 73 during the series of blood pressure measurement period.

The measurement result of the continuous blood pressure by the blood pressure determining unit 108 is displayed on the display unit 40 or is stored in the flash memory 43.

Figures 5A, 5B:
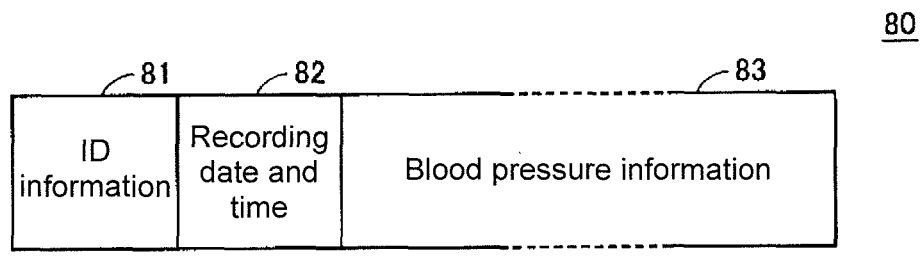
FIGS. 5A and 5B are views showing data structure examples of each measurement data according to one or more embodiments of the present invention.

The data structure example of each measurement data stored in the flash memory 43 is shown in FIGS. 5A and 5B.

FIG. 5A is a view showing a data structure of each measurement data in one or more embodiments of the present invention.

With reference to FIG. 5A, each measurement data 80 stored in the flash memory 43 includes three fields 81 to 83 of "ID information", "recording date and time", and "blood pressure information" as an example. Schematically describing the content of each field, the "ID information" field 81 stores the identification number or the like for specifying each measurement data, and the "recording date and time" field 82 stores information such as the measurement start date and the measurement period of each measurement data timed by the timing unit 45. The "blood pressure information" field 83 stores the blood pressure data of time series, that is, the blood pressure waveform data.

FIG. 5B is a view showing a data structure of the blood pressure information field 83 contained in the measurement data. With reference to FIG. 5B, the blood pressure information field 83 includes a region 831 for storing "time data" and a region 832 for storing "blood pressure data".

The region 831 stores a plurality of time data 1, 2, 3, ... N corresponding to the sampling period. The region 832 stores the blood pressure data BD (1), BD (2), ..., BD (n) in correspondence with each time data of the region 831. In the region 832, the region indicated with "−" means that the difference between the value of the arterial volume and the target value at the relevant time point exceeded a predetermined value and is not recorded as the blood pressure or that the adjustment of the control amount by the adjustment processing unit 112 is carried out.

The storage mode is not limited to such example, and the time (hour) and the blood pressure merely need to be stored in correspondence to each other.

Therefore, the blood pressure information is stored in the flash memory 43. The blood pressure information may include indices that can be calculated from the pulse wave such as the pulse rate and the AI, other than the blood pressure value such as the systolic blood pressure, the diastolic blood pressure, or the average blood pressure.

According to one or more embodiments of the present invention, the operation of each function block is realized by executing the software stored in the memory 42, but at least one of such function blocks may be realized by hardware.

<Regarding Operation>

Figure 6:
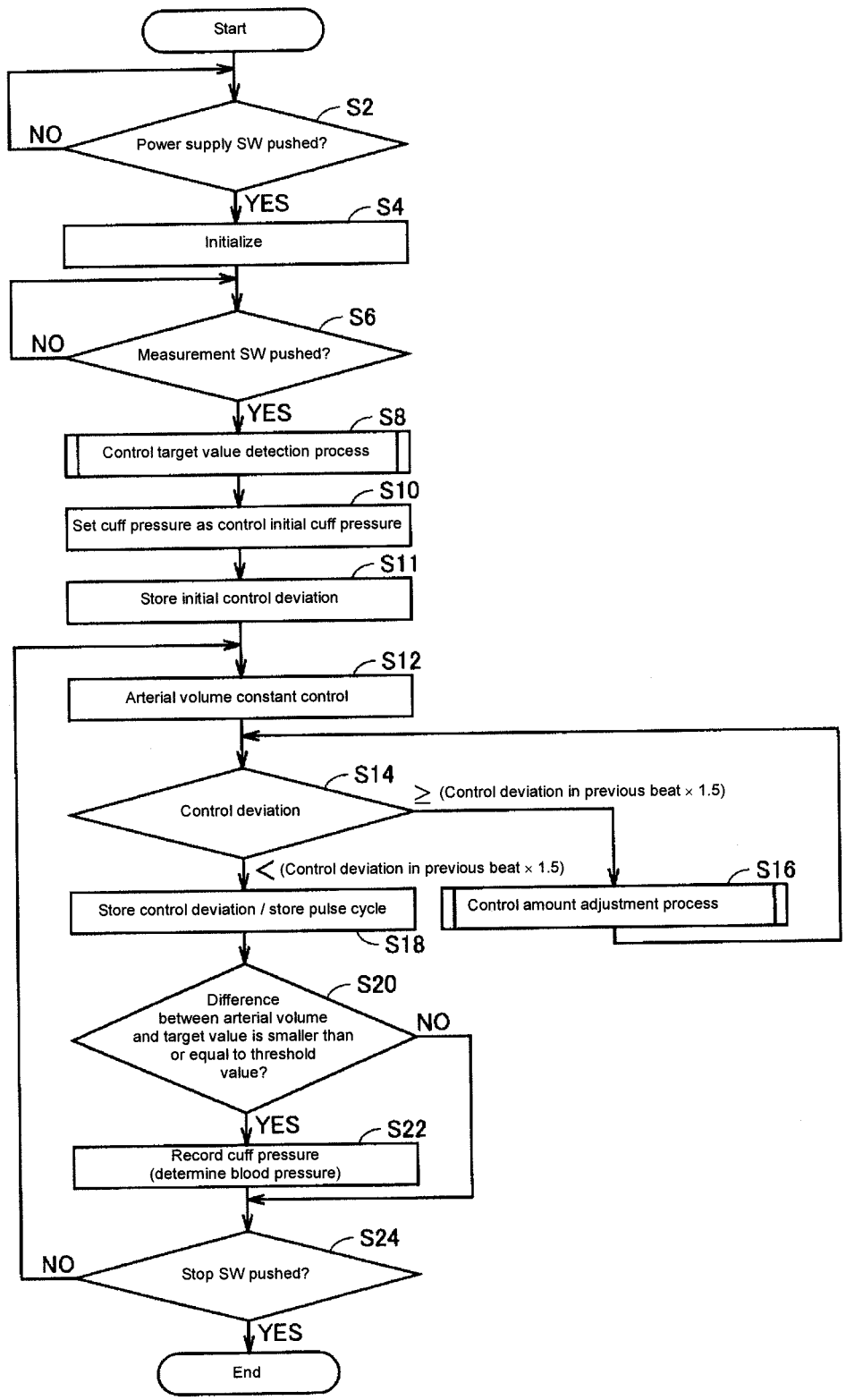
FIG. 6 is a flowchart showing the blood pressure measurement process according to one or more embodiments of the present invention.

FIG. 6 is a flowchart showing the blood pressure measurement process according to one or more embodiments of the present invention. The process shown in the flowchart of FIG. 6 is stored in the memory 42 as a program in advance, and the function of the blood pressure measurement process is realized when the CPU 100 reads out and executes such program.

With reference to FIG. 6, the CPU 100 determines whether or not the power supply switch 41A is pushed (step S2). If determined that the power supply switch 41A is pushed (YES in step S2), the process proceeds to step S4.

In step S4, the CPU 100 performs the initialization process. Specifically, a predetermined region of the memory 42 is initialized, the air of the air bladder 21 is exhausted, and the 0 mmHg correction of the pressure sensor 32 is carried out.

After the initialization is finished, the CPU 100 determines whether or not the measurement switch 41B is pushed (step S6). The CPU 100 waits until the measurement switch 41B is pushed. When determined that the measurement switch 41B is pushed (YES in step S6), the process proceeds to step S8.

In step S8, the target value detection unit 104 executes the control target value detection process. In other words, the control target value and the initial cuff pressure are determined. The control target value detection process will be described using FIG. 7 and FIG. 8.

Figure 7:
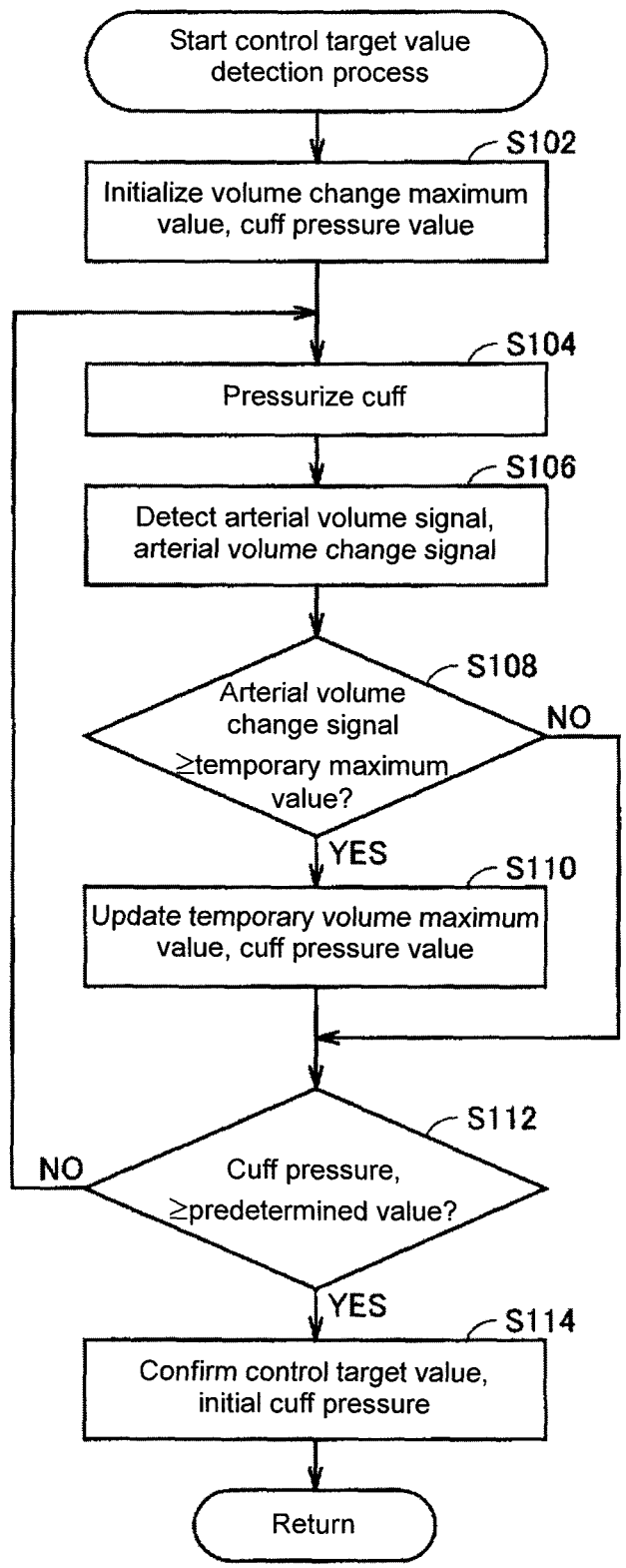
FIG. 7 is a flowchart showing the control target value detection process according to one or more embodiments of the present invention.
Figure 8:
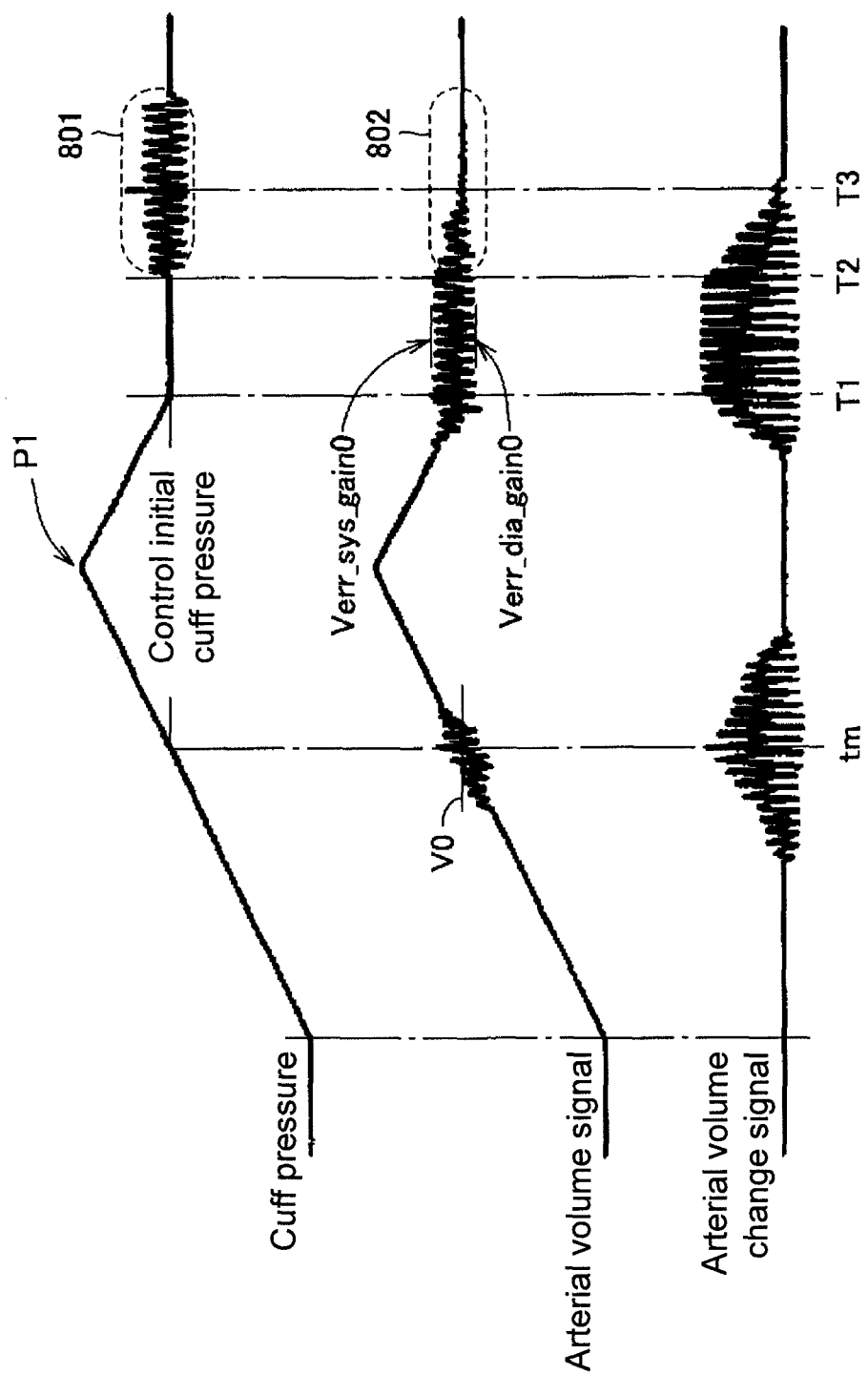
FIG. 8 is a view describing the blood pressure measurement process according to one or more embodiments of the present invention.

FIG. 7 is a flowchart showing the control target value detection process in one or more embodiments of the present invention. FIG. 8 is a view describing the blood pressure measurement process of one or more embodiments of the present invention. FIG. 8 shows the cuff pressure, the arterial volume signal, and the arterial volume change signal along the common time axis.

The arterial volume change signal can be obtained by filtering the arterial volume signal. The filtering of the arterial volume signal may be carried out in the arterial volume detection circuit 74 or may be carried out by the CPU 100.

With reference to FIG. 7, the target value detection unit 104 initializes the maximum value (volume change maximum value) of the arterial volume change signal and the cuff pressure value stored in a predetermined region of the memory 42 (step S102). The initialization of the arterial volume value is also carried out.

In the following process, the maximum value of the arterial volume change signal is updated as needed, and hence, the value until ultimately confirmed as a maximum value is referred to as "temporary volume maximum value".

The pump drive circuit 53 is then drive controlled to pressurize the cuff pressure (step S104).

At the stage of pressurizing the cuff pressure, the target value detection unit 104 detects the signal (arterial volume signal) from the arterial volume detection circuit 74 (step S106). The target value detection unit 104 detects the arterial volume change signal obtained from the arterial volume signal.

The target value detection unit 104 determines whether or not the value of the arterial volume change signal is greater than or equal to the temporary volume maximum value stored in the memory 42 (step S108). If determined that the value of the arterial volume change signal is greater than or equal to the temporary volume maximum value (YES in step S108), the process proceeds to step S110. If determined that the arterial volume change signal is smaller than the temporary volume maximum value (NO in step S108), the process proceeds to step S112.

In step S110, the target value detection unit 104 updates the temporary volume maximum value, and overwrites and records the cuff pressure at the relevant time point. After this process is finished, the process proceeds to step S112.

In step S112, the target value detection unit 104 determines whether or not the cuff pressure is greater than or equal to a predetermined value (point P1 in FIG. 8). If determined that the cuff pressure has not reached a predetermined value (NO in step S112), the process returns to step S104. If determined that the cuff pressure is greater than or equal to the predetermined value (YES in step S112), the process proceeds to step S114.

In step S114, the target value detection unit 104 confirms the temporary volume maximum value ultimately recorded in step S110 as the maximum value, and confirms the cuff pressure value at time point tm at which the maximum value is detected as the initial cuff pressure. The target value detection unit 104 confirms the average value, or the like of the arterial volume signal at time point tm as a control target value (V0).

The target value detection unit 104 stores the detected initial cuff pressure and the control target value in a predetermined region of the memory 42.

After the process of step S114 is finished, the process is returned to the main routine.

Again referring to FIG. 6, the servo control unit 106 sets the cuff pressure to the initial cuff pressure when the control target value and the initial cuff pressure are determined (step S10). At this time point, the control gain for the servo control is an initial value (e.g., 0).

When the cuff pressure is set to the initial cuff pressure, the CPU 100 stores the control deviation at the time in a predetermined region of the memory 42 as an initial control deviation (step S11). Specifically, the control deviation on the systolic blood pressure side ("Verr_sys_gain0" in FIG. 8) and the control deviation on the diastolic blood pressure side ("Verr_dia_gain0" in FIG. 8) are temporarily recorded.

Each initial deviation may be a statistical value (e.g., average value or maximum value) of the arterial volume level for a plurality of beats. It may also be an arterial volume level of a predetermined beat.

The servo control unit 106 starts the arterial volume constant control so that the arterial volume signal and the control target value match (step S12). That is, the cuff pressure is feedback controlled so that the value of the arterial volume change signal becomes substantially zero by controlling the pressure adjustment unit 50.

The servo control unit 106 detects the control gain (proportional gain) to be used in the servo control. Specifically, the control gain is gradually increased from the initial value (e.g., 0) to detect the control gain most suited to the person to be measured.

In order to determine the optimum control gain during the control, a method described in "Yamakoshi K, Shimazu H, Togawa T, Indirect measurement of instantaneous arterial blood pressure in the rat, AMJ Physiol 237, H632-H637, 1979" may be used. In other words, the control gain of when the erasing rate of the arterial volume change signal (amplitude during control/amplitude before control) becomes smaller than a predetermined value may be determined as an optimum control gain.

According to one or more embodiments of the present invention, the (optimum) control gain used in the servo control is referred to as "appropriate gain".

According to one or more embodiments of the present invention, the appropriate gain is determined during the control, but is not limited thereto. The appropriate gain may be determined beforehand. That is, the time (waste time) required until the output value starts to respond when the input value is fluctuated in a step-wise manner, and the speed (time constant) of change from when it started to respond may be measured in advance, and the control gain may be determined based on such values.

When the arterial volume constant control starts, the fluctuation detection unit 110 detects the control deviation for every beat (maximum value and minimum value of control deviation). Whether or not the respective control deviation on the systolic blood pressure side and the diastolic blood pressure side is smaller than a predetermined magnification (e.g., 1.5 times) of the control deviation in the previous beat is determined (step S14). Therefore, whether or not a rapid fluctuation occurred in the control deviation, that is, whether or not a rapid fluctuation occurred in the arterial volume signal is determined.

Whether or not the first beat after the start of the arterial volume constant control is smaller than a predetermined magnification (e.g., ½ times) of the initial control deviation (Verr_sys_gain0, Verr_dia_gain0) may be determined.

According to one or more embodiments of the present invention, the threshold value on whether or not a rapid (abnormal) fluctuation occurred is set as 1.5 times the control deviation in the previous beat, but is not limited thereto as long as the measurement site is not excessively compressed.

If determined that both current control deviations are smaller than 1.5 times the control deviation in the previous beat in step S14 ("<(control deviation in previous beat×1.5)" in step S14), the process proceeds to step S18 assuming rapid fluctuation has not occurred.

If determined that at least one of the current control deviation is greater than or equal to 1.5 times the control deviation in the previous beat "≥(control deviation in previous beat× 1.5)" in step S14, the process proceeds to step S16 assuming rapid fluctuation occurred.

Even if the control deviation of this time is determined as smaller than 1.5 times the control deviation in the previous beat, determination is made that there is a high possibility that noise exists if the control deviation of this time exceeds a predetermined magnification (e.g., 1.5 times) the initial control deviation (Verr_sys_gain0, Verr_dia_gain0), and the process proceeds to step S16.

In step S16, the control amount adjustment process is executed. The control amount adjustment process will be described in detail later.

After the control amount adjustment process is finished, the process returns to step S14, and the presence or absence of rapid change is again detected.

In step S18, the fluctuation detection unit 110 stores the current control deviation in a predetermined region of the memory 42. Only the most recent control deviation may be updated and stored. The pulse cycle may be updated and stored with the control deviation. The pulse cycle is used in the control amount adjustment process.

In parallel to the arterial volume constant control, the blood pressure determining unit 108 determines whether or not a difference between the arterial volume (value indicating arterial volume signal) and the control target value is smaller than or equal to a predetermined threshold value (step S20). Alternatively, whether or not the value of the volume change signal is close to zero (smaller than or equal to a predetermined threshold value) may be determined.

If determined that the difference between the arterial volume and the control target value is smaller than or equal to the threshold value (YES in step S20), the blood pressure determining unit 108 determines the cuff pressure in this case as the blood pressure, and stores the same in the flash memory 43 (step S22). During the measurement, the blood pressure data is stored in the memory 42, and the blood pressure data stored in the memory 42 may be copied to the flash memory 43 at the time point the series of measurement processes is terminated.

The process proceeds to step S24 after the process of step S22 is finished.

If determined that the difference between the arterial volume and the control target value exceeds the predetermined threshold value (NO in step S20), the process proceeds to step S24. That is, if the arterial volume and the control target value cannot be considered as substantially matching, the cuff pressure in this case is not determined as the blood pressure value.

In step S24, the servo control unit 106 determines whether or not the stop switch 41C is pushed. If determined that the stop switch 41C is not pushed (NO in step S24), the process returns to step S12. If determined that the stop switch 41C is pushed (YES in step S24), the series of blood pressure measurement process is terminated.

According to one or more embodiments of the present invention, the blood pressure measurement process is terminated when the pushing of the stop switch 41C is detected, but may be terminated after elapse of a predetermined time from the start of the arterial volume constant control.

(Regarding Control Amount Adjustment Process)

The control amount adjustment process executed in step S16 of FIG. 6 will now be described in detail.

Figure 9:
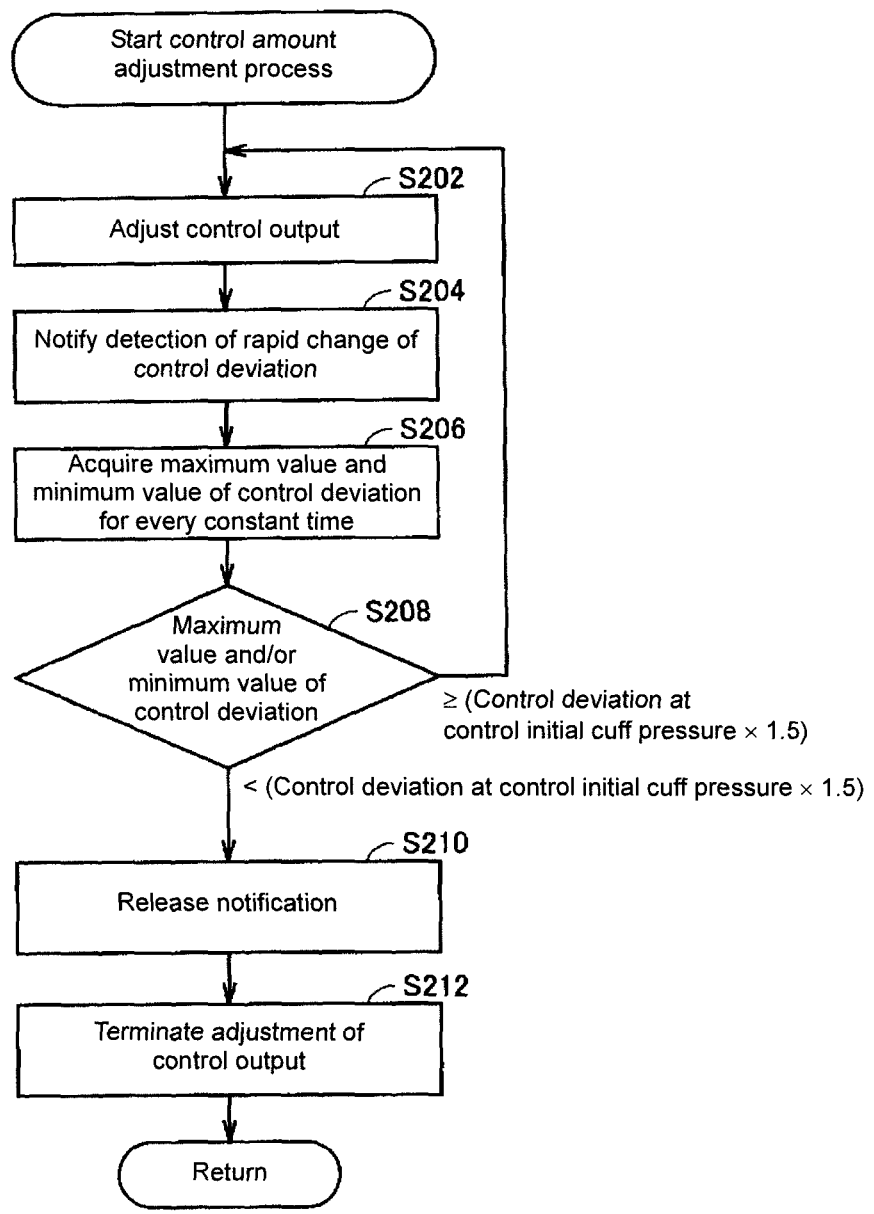
FIG. 9 is a flowchart showing the control amount adjustment process in one or more embodiments of the present invention.

FIG. 9 is a flowchart showing the control amount adjustment process in one or more embodiments of the present invention.

With reference to FIG. 9, the adjustment processing unit 112 sets the control gain to the initial value to adjust the control output (step S202). That is, the adjustment processing unit 112 sets the control gain of the proportional control by the servo control unit 106 to 0. The change in control amount by the servo control unit 106 is thus eliminated, and the cuff pressure is fixed to substantially the initial cuff pressure.

When rapid fluctuation of the arterial volume signal (i.e., abnormal increase or decrease of arterial volume signal) occurs during the feedback control, the cuff pressure excessively rises in response thereto. As a result, the measurement site is compressed in excess, and the person to be measured may feel pain. According to one or more embodiments of the present invention, the rapid fluctuation of arterial volume signal is detected at the initial stage and the control gain is immediately returned to the initial value, so that the control amount can be adjusted before the excessive response occurs.

The "excessive response" refers to a response larger than the response caused by only the change of the arterial volume involved in pulsation, that is, a response of when the noise such as body motion is superimposed on the arterial volume signal.

According to one or more embodiments of the present invention, the excessive response is suppressed (eliminated) by setting the control gain to the initial value. However, it is not limited to the initial value as long as the excessive response can be suppressed. That is, it is not limited to the initial value if the pressure adjustment unit 50 is controlled so as to be smaller than or equal to the control amount in the normal state before the rapid fluctuation is detected.

The form is not limited to the form of suppressing the excessive response by changing the control gain. For instance, the feedback control itself may be cancelled by assuming a predetermined control output not dependent on the control deviation. In this case, the adjustment processing unit 112 may output an instruction signal to the servo control unit 106 to cancel the feedback control and set the cuff pressure to the initial cuff pressure.

At the same time as when the adjustment of the control output is carried out, the adjustment processing unit 112 notifies that the rapid change of the control deviation (rapid change of arterial volume) is detected (step S204). For instance, a predetermined mark may be displayed on the display unit 40, and such mark may be lighted to notify that the rapid change of the control deviation (abnormal increase) occurred. An alarm sound may be emitted by the buzzer 47.

Thereafter, the adjustment processing unit 112 may acquire the maximum value and the minimum value of the control deviation for every predetermined time (step S206). According to one or more embodiments of the present invention, the maximum value and the minimum value of the control deviation may be extracted for every pulse cycle stored in step S18 of FIG. 6 as a constant time. The constant time merely needs to be a time sufficiently long with respect to the noise such as two seconds.

Whether or not the maximum value and the minimum value of the control deviation are respectively smaller than a predetermined magnification (e.g., 1.5) of the control deviation at the control initial cuff pressure, that is, the initial control deviation (step S208), may be determined. The initial control deviation (Verr_sys_gain0, Verr_dia_gain0) is stored in the memory 42 in step S11 of FIG. 6.

If at least one of the maximum value or the minimum value of the control deviation is greater than or equal to 1.5 times the control deviation at the control initial cuff pressure (≥"control deviation at control initial cuff pressure×1.5" in step S208), the process is returned to step S202, and the adjustment of the control output is continued.

When detected that both the maximum value and the minimum value of the control deviation are smaller than 1.5 of the control deviation at the control initial cuff pressure (<"control deviation at control initial cuff pressure×1.5" in step S208), determination is made that the rapid fluctuation of the control deviation converged and the process proceeds to step S210.

In step S210, the adjustment processing unit 112 releases the notification (step S210) and returns the control output to original (step S212). That is, the control gain set at the initial value is again set to the appropriate gain. The feedback control is thereby restored.

If a predefined time (e.g., 30 seconds) continued and determined that the control deviation is greater than or equal to 1.5 times of the initial control deviation in step S208, the blood pressure measurement process may be terminated.

The detection of rapid change and the adjustment of control output will be described using specific examples.

FIGS. 10A and 10B are views describing the detection of the rapid change of the arterial volume and the adjustment process of the control output in one or more embodiments of the present invention.

FIG. 10A shows a control deviation along the time axis. That is, the level (unit of vertical axis: V) of the arterial volume signal (obtained from arterial volume detection circuit 74) having the control target value as a reference is shown. The graph of FIG. 10A shows one part (after time T3)

of the arterial volume signal in a zone indicated with reference numeral 802 in FIG. 8 in an enlarged manner.

FIG. 10B shows the control amount along the same time axis as FIG. 10A. That is, the level (unit of vertical axis: mmHg) of the cuff pressure signal (obtained from oscillation circuit 33) having the initial cuff pressure as a reference is shown. The graph of FIG. 10B shows one part (after time T3) of the cuff pressure signal in a zone indicated with reference numeral 801 in FIG. 8 in an enlarged manner.

With reference to FIG. 10A, comparison is carried out with the control deviation of the previous beat for every one beat during the period of the arterial volume constant control, and the normal feedback control is performed if the current control deviation is smaller than 1.5 times the control deviation of the previous beat. That is, whether or not the minimum value and the maximum value of the current control deviation are respectively smaller than 1.5 times the minimum value Verr_dia and the maximum value Verr_sys of the control deviation of the previous beat is determined. If both are smaller than 1.5 times the value of the previous beat, the normal feedback control is performed. In such a case, the waveform indicating the change of the control amount is assumed to be substantially equal to the blood pressure waveform, as indicated with the waveform up to time TA of FIG. 10B.

When the minimum value of the current control deviation becomes greater than or equal to 1.5 times the minimum value Verr_dia of the control deviation of the previous beat, or when the maximum value of the current control deviation becomes greater than or equal to 1.5 times the maximum value Verr_sys of the control deviation of the previous beat, the control gain is immediately set to the initial value. In such a case, the control amount is fixed at 0, as indicated with the waveform from time TA to TB in FIG. 10B. That is, the cuff pressure is set to the initial cuff pressure, similar to the zone of time T1 to T2 in FIG. 8.

Even if the arterial volume rapidly fluctuates by body motion or the like, the fluctuation can be detected at the initial stage by continuously monitoring the control deviation. Therefore, the control amount can be adjusted before excessively (rapidly) compressing the cuff. As a result, the burden on the person to be measured due to the excessive compression on the measurement site can be eliminated.

Furthermore, the control deviation is monitored even during the adjustment of the control amount, and whether or not both control deviations on the systolic blood pressure side and the diastolic blood pressure side are smaller than 1.5 times the initial control deviation (Verr_sys_gain0, Verr_dia_gain0) may be detected. If both are smaller than 1.5 times the initial control deviation, determination is made that the rapid fluctuation (rapid change) converged and the control gain is returned to the original appropriate gain.

Therefore, according to one or more embodiments of the present invention, the feedback control can be automatically restored if the abnormal fluctuation of the control deviation converges even if the rapid change of the control deviation is detected during the blood pressure measurement. Therefore, the measurement does not need to be redone, and the trouble of the user is not required.

When the rapid change of the control deviation is detected, this is notified to the user until the control deviation converges. Therefore, the user can grasp that the blood pressure being displayed is not correct. The user can also recognize that the possibility the measurement posture is unbalanced. As a result, the accurate blood pressure measurement can be carried out after the measurement position is corrected.

According to one or more embodiments of the present invention, the control deviation is stored for every one beat, and the control deviation of this time and the control deviation for the previous beat are compared. If there is fluctuation in the blood pressure, the output of the arterial volume also shifts to the upper side, and then returns to the original. Therefore, the rapid fluctuation of the arterial volume can be reliably detected at the initial stage by comparing with the control deviation of the previous time each time.

However, not limited to the above, the average value of the control deviation may be stored for every plural beats, and the control deviation of this time and the stored control deviation may be compared.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF REFERENCE NUMERALS

1 blood pressure information measurement device
10 main body
20 cuff
21 air bladder
30 air system
31 air tube
32 pressure sensor
33 oscillation circuit
40 display unit
41 operation unit
41A power supply switch
41B measurement switch
41C stop switch
41D memory switch
42 memory
43 flash memory
44 power supply
45 timing unit
46 interface unit
47 buzzer
50 pressure adjustment unit
51 pump
52 valve
53 pump drive circuit
54 valve drive circuit
70 arterial volume sensor
71 light emitting element
72 light receiving element
73 light emitting element drive circuit
74 arterial volume detection circuit
75 arterial volume measuring unit
100 CPU
104 target value detection unit
106 servo control unit
108 blood pressure determining unit
110 fluctuation detection unit
112 adjustment processing unit
132 recording medium

The invention claimed is:
1. A blood pressure information measurement device that measures blood pressure information by detecting a volume of an artery, the blood pressure information measurement device comprising:

a cuff to be wrapped around a predetermined measurement site;

a pressure adjustment unit that adjusts a pressure of the cuff by pressurization and depressurization;

a pressure detection unit that detects a cuff pressure representing the pressure of the cuff;

a volume detection unit, arranged at a predetermined position of the cuff, that detects an arterial volume signal indicating the volume of the artery;

a detection processing unit that detects a control target value based on the arterial volume signal;

a servo control unit that performs a servo control of the pressure adjustment unit so that a value of the arterial volume signal matches the control target value; and a fluctuation detection unit that detects a rapid fluctuation of the arterial volume signal at an initial stage during a period of the servo control, wherein the fluctuation detection unit determines that the rapid fluctuation occurred when a control deviation representing a level of the arterial volume signal having the control target value as a reference becomes greater than or equal to a predetermined magnification of a reference deviation, and wherein the blood pressure information measurement device further comprises an adjustment processing unit that adjusts a control amount of the pressure adjustment unit by the servo control unit so that an excessive response is not made when the rapid fluctuation is detected by the fluctuation detection unit.

2. The blood pressure information measurement device according to claim 1, wherein the adjustment processing unit continues the adjustment of the control amount until the rapid fluctuation of the arterial volume signal converges.

3. The blood pressure information measurement device according to claim 2, wherein the adjustment processing unit determines that the rapid fluctuation converged when the control deviation becomes smaller than a predetermined magnification of an initial control deviation before performing the servo control at an appropriate gain for a predetermined period.

4. The blood pressure information measurement device according to claim 3, wherein the detection processing unit detects an initial cuff pressure representing a reference cuff pressure in the servo control, and wherein the initial control deviation is an initial value which control gain is lower than the appropriate gain, and represents the control deviation when the cuff pressure is set to the initial cuff pressure.

5. The blood pressure information measurement device according to claim 4, wherein the adjustment processing unit adjusts the control amount of the pressure adjustment unit by setting the control gain to the initial value.

6. The blood pressure information measurement device according to claim 4, wherein the adjustment processing unit adjusts the control amount of the pressure adjustment unit by setting the cuff pressure to the initial cuff pressure.

7. The blood pressure information measurement device according to claim 1, wherein the reference deviation is defined in advance as the control deviation of one or more beats earlier.

8. The blood pressure information measurement device according to claim 1, further comprising a blood pressure determining unit that determines a cuff pressure when a difference between the value of the arterial volume signal and the control target value is smaller than or equal to a threshold value defined in advance as the blood pressure.

* * * * *